United States Patent [19]
Shropshire

[11] Patent Number: 5,882,256
[45] Date of Patent: Mar. 16, 1999

[54] FRAGRANCE DISPENSER

[76] Inventor: Maurice C. Shropshire, 3680 N. Orangewood Ave., Rialto, Calif. 92377

[21] Appl. No.: 871,691

[22] Filed: Jun. 9, 1997

[51] Int. Cl.⁶ ..................................................... B60H 3/00
[52] U.S. Cl. ........................................... 454/157; 422/124
[58] Field of Search ............................ 454/157; 422/123, 422/124

[56] References Cited

U.S. PATENT DOCUMENTS

| 4,867,045 | 9/1989 | Freedman | 454/157 |
| 4,913,034 | 4/1990 | Ripple et al. | 454/157 |
| 5,078,046 | 1/1992 | Mascolo et al. | 454/157 |
| 5,186,869 | 2/1993 | Stumpf et al. | 422/124 X |
| 5,567,361 | 10/1996 | Harper | 422/124 X |

FOREIGN PATENT DOCUMENTS

| 32 09 698 | 10/1983 | Germany | 422/124 |
| 63-279922 | 11/1988 | Japan | 454/157 |

*Primary Examiner*—Harold Joyce

[57] ABSTRACT

A fragrance dispenser including a fragrance container for housing a predetermined amount of liquid fragrance. A dispensing mechanism is included for dispensing the fragrance upon the receipt of power. Also provided is a manual actuation switch for allowing the single and immediate transfer of power to the dispensing mechanism upon the depression thereof. Finally, the manual actuation switch is connected to an ignition of the vehicle for being capable of transferring power only when the vehicle is activated.

1 Claim, 1 Drawing Sheet

FRAGRANCE DISPENSER

BACKGROUND OF THE INVENTION

1. Field of the Invention

The present invention relates to a fragrance dispenser and more particularly pertains to dispensing fragrance within a vehicle.

2. Description of the Prior Art

The use of fragrance dispensers is known in the prior art. More specifically, fragrance dispensers heretofore devised and utilized for the purpose of eliminating odors are known to consist basically of familiar, expected and obvious structural configurations, notwithstanding the myriad of designs encompassed by the crowded prior art which have been developed for the fulfillment of countless objectives and requirements.

By way of example, the prior art includes U.S. Pat. No. 5,038,972 to Muderlak et al.; U.S. Pat. No. 5,249,718 to Muderlak; U.S. Pat. No. Des. 357,977 Muderlak; U.S. Pat. No. 5,449,117 to Muderlak et al.; U.S. Pat. No. 5,105,133 to Yang; and U.S. Pat. No. 4,830,791 to Muderlak et al.

In this respect, the fragrance dispenser according to the present invention substantially departs from the conventional concepts and designs of the prior art, and in so doing provides an apparatus primarily developed for the purpose of dispensing fragrance within a vehicle.

Therefore, it can be appreciated that there exists a continuing need for a new and improved fragrance dispenser which can be used for dispensing fragrance within a vehicle. In this regard, the present invention substantially fulfills this need.

SUMMARY OF THE INVENTION

In view of the foregoing disadvantages inherent in the known types of fragrance dispensers now present in the prior art, the present invention provides an improved fragrance dispenser. As such, the general purpose of the present invention, which will be described subsequently in greater detail, is to provide a new and improved fragrance dispenser which has all the advantages of the prior art and none of the disadvantages.

To attain this, the present invention essentially comprises a fragrance container having a cylindrical configuration with a circular top face, a circular bottom face, and a periphery formed therebetween defining an interior space. As shown in FIG. 2, the container includes a dispensing tube vertically disposed within the interior space of the container and extended through the top face thereof. The dispensing tube has a first end situated within the interior space of the container adjacent the bottom face thereof. The first end is equipped with a plurality of apertures formed therein. The dispensing tube also has a second end positioned exterior of the container. As such, the container holds a predetermined amount of liquid fragrance and the top face of the container is removably coupled to the periphery such that the container may be refilled when necessary. With reference still to FIG. 2, a pump is mechanically connected to the second end of the dispensing tube. The pump comprises a dispensing nozzle connected thereto which is preferably situated below a dash of a vehicle. In use, the pump is adapted to spray the liquid fragrance from the dispensing nozzle upon the receipt of power. Further provided is a fan situated behind the dispensing nozzle for dispersing the liquid fragrance sprayed by the pump upon the receipt of power. Situated within a reach of a user of the vehicle is a control panel having a rectangular configuration. A fragrance low level detection means is provided with a liquid switch situated within the interior space of the container. It is imperative that the switch be situated a predetermined distance from the bottom face of the container. In operation, the liquid switch is adapted for emitting a low level signal upon the lack of detection of liquid. The fragrance low level detection means further includes a light emitting diode situated on a front face of the control panel for emitting a light upon the receipt of the fragrance low level signal. Positioned on the front face of the control panel is a manual actuation switch. The manual activation switch is adapted for allowing the single and immediate transfer of power to the fan and pump upon the depression thereof. Associated therewith is a delay actuation switch also situated on the front face of the control panel. The delay actuation switch is connected to delay control means positioned within the control panel. The delay control means is adapted for allowing the intermittent transfer of power to the pump and fan upon the depression of the delay actuation switch. For controlling the transfer of power to the pump and fan, central control means is positioned within the control panel and connected between the pump and fan and the manual actuation switch and the delay actuation switch and delay control means. The central control means is capable of allowing the transfer of the power to the fan and pump from at least one of the switches upon the depression thereof. In addition, it is further designed to govern each transfer of power such that they are of a constant predetermined magnitude and duration. Finally, it is imperative that the manual actuation switch and delay actuation switch are both connected to an ignition of the vehicle for being capable of transferring power only when the vehicle is activated.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved fragrance dispenser which has all the advantages of the prior art fragrance dispensers and none of the disadvantages.

It is another object of the present invention to provide a new and improved fragrance dispenser which may be easily and efficiently manufactured and marketed.

It is a further object of the present invention to provide a new and improved fragrance dispenser which is of a durable and reliable construction.

An even further object of the present invention is to provide a new and improved fragrance dispenser which is susceptible of a low cost of manufacture with regard to both materials and labor, and which accordingly is then susceptible of low prices of sale to the consuming public, thereby making such fragrance dispenser economically available to the buying public.

Still yet another object of the present invention is to provide a new and improved fragrance dispenser which provides in the apparatuses and methods of the prior art some of the advantages thereof, while simultaneously overcoming some of the disadvantages normally associated therewith.

Still another object of the present invention is to dispense fragrance within a vehicle.

Lastly, it is an object of the present invention to provide a new and improved fragrance dispenser including a fragrance container for housing a predetermined amount of liquid fragrance. A dispensing mechanism is included for dispensing the fragrance upon the receipt of power. Also provided is a manual actuation switch for allowing the single and immediate transfer of power to the dispensing mechanism upon the depression thereof. Finally, the manual actuation switch is connected to an ignition of the vehicle for being capable of transferring power only when the vehicle is activated.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

Similar reference characters refer to similar parts throughout the several views of the drawings.

DESCRIPTION OF THE PREFERRED EMBODIMENT

Figure 1:
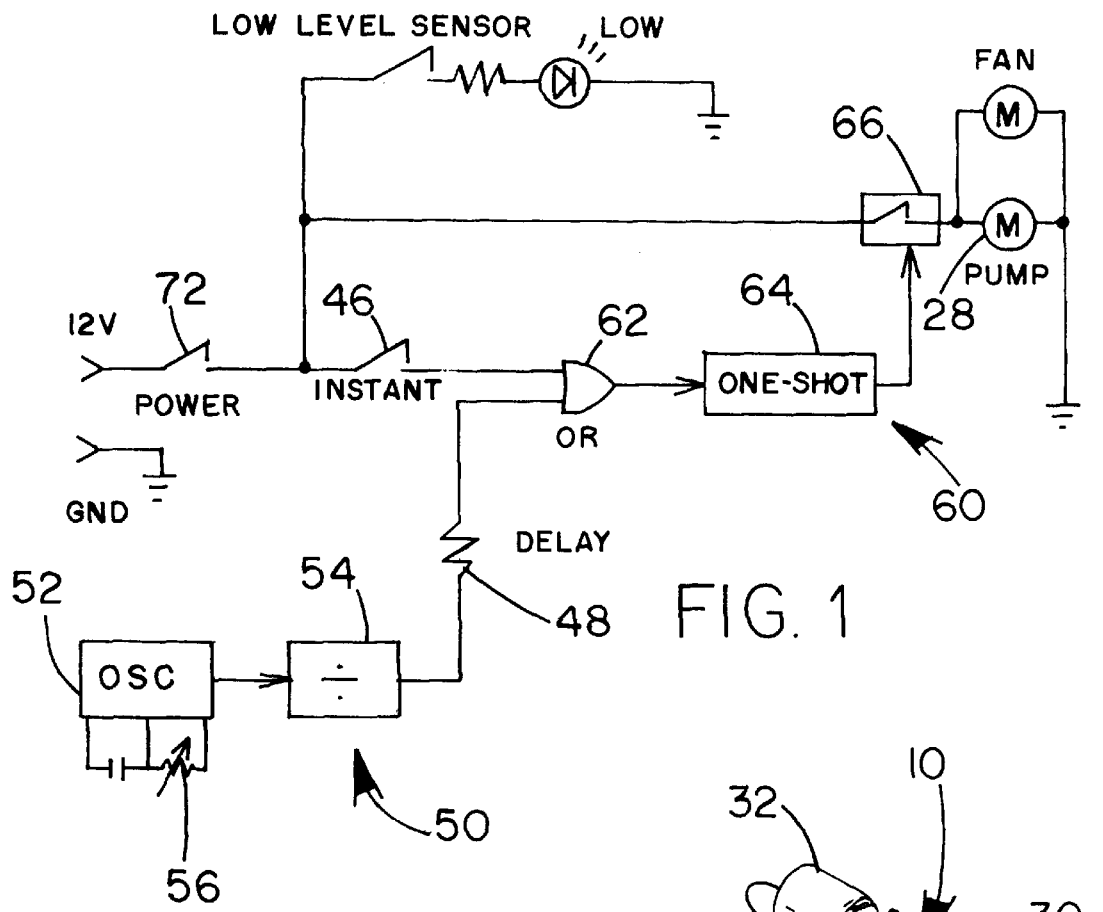
FIG. 1 is a schematic diagram of the interconnection of various electrical components of the present invention.

With reference now to the drawings, and in particular to FIG. 1 thereof, a new and improved fragrance dispenser embodying the principles and concepts of the present invention and generally designated by the reference numeral 10 will be described.

The present invention, the new and improved fragrance dispenser, is comprised of a plurality of components. Such components in their broadest context include a container, pump, fan, low level detection means, manual actuation switch, and delay actuation switch. Such components are individually configured and correlated with respect to each other so as to attain the desired objective.

Figure 2:
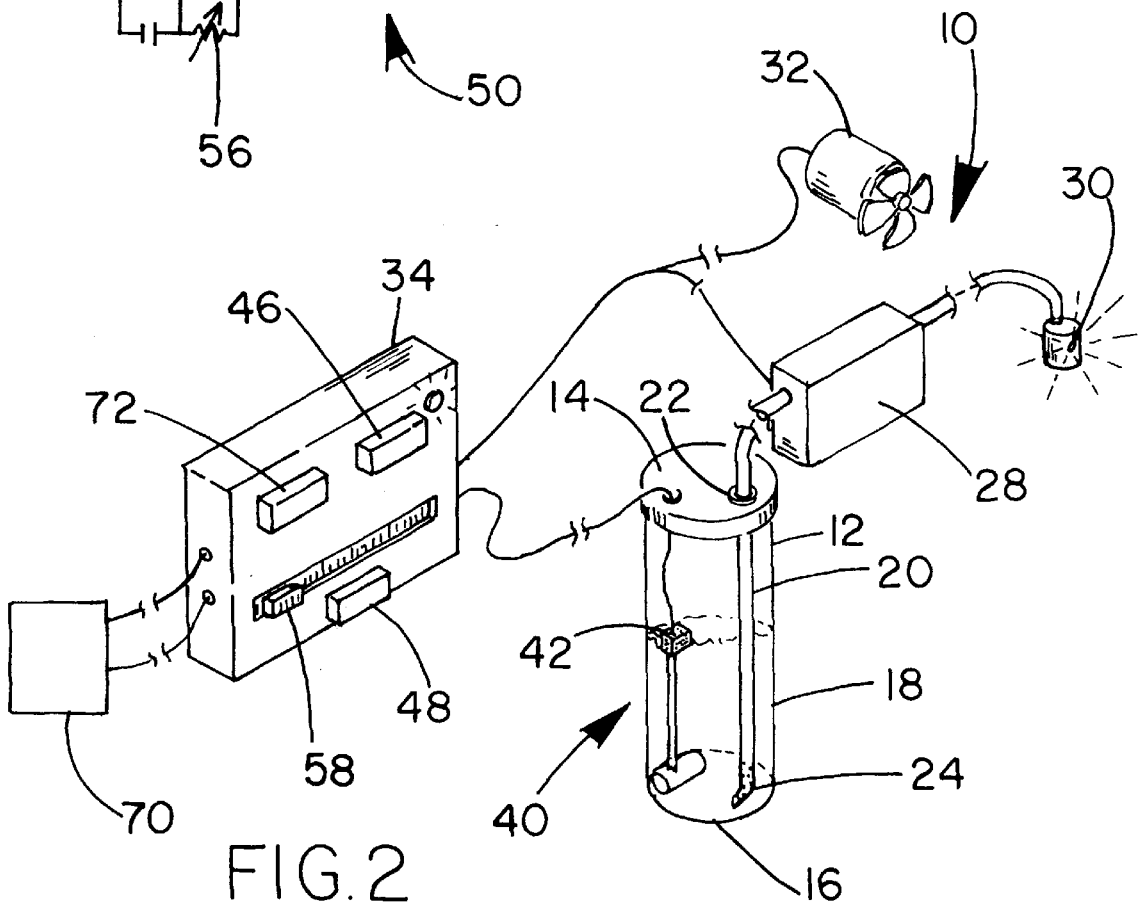
FIG. 2 is a perspective view of the entire system of the present invention.

More specifically, it will be noted that the system 10 of the present invention includes a fragrance container 12 having a cylindrical configuration with a circular top face 14, a circular bottom face 16, and a periphery 18 formed therebetween defining an interior space. As shown in FIG. 2, the container includes a dispensing tube 20 vertically disposed within the interior space of the container and extended through the top face thereof. Ideally, the aperture that the dispensing tube passes through is lined with a gasket 22 for preventing leakage. The dispensing tube has a first end situated within the interior space of the container adjacent the bottom face thereof. The first end is equipped with a plurality of apertures 24 formed therein. The dispensing tube also has a second end positioned exterior of the container. As such, the container holds a predetermined amount of liquid fragrance and the top face of the container is removably coupled to the periphery such that the container may be refilled when necessary.

With reference still to FIG. 2, a pump 28 is mechanically connected to the second end of the dispensing tube. The pump comprises a dispensing nozzle 30 connected thereto which is preferably situated below a dash of a vehicle. In use, the pump is adapted to spray the liquid fragrance from the container through the dispensing nozzle upon the receipt of power. Further provided is a fan 32 situated behind the dispensing nozzle for dispersing the liquid fragrance sprayed by the pump upon the receipt of power.

Situated within a reach of a user of the vehicle is a control panel 34 having a rectangular configuration. In the alternative, the contents of the control panel may be incorporated directly into the dash of the vehicle.

A fragrance low level detection means 40 is provided with a liquid switch 42 situated within the interior space of the container. It is imperative that the switch be situated a predetermined distance from the bottom face of the container. In operation, the liquid switch is adapted for emitting a fragrance low level signal upon the lack of detection of liquid. The fragrance low level detection means further includes a light emitting diode 44 situated on a front face of the control panel for emitting a light upon the receipt of the fragrance low level signal. It should be noted that the liquid switch is conventional in nature and, accordingly, opens upon the lack of detection of liquid. As such, it is necessary to incorporate accompanying circuitry which is adapted effect a closing of a switch when the liquid switch no longer detects liquid. Such circuitry is conventionally know and readily available. For example, a relay with a contact that is normally closed may be maintained open while the liquid switch is closed by providing power to an associated coil. When the relay coil ceases to receive power upon the opening of the liquid switch, the contact will close.

Positioned on the front face of the control panel is a manual actuation switch 46. The manual activation switch is adapted for allowing the single and immediate transfer of power to the fan and pump upon the instant depression thereof.

Associated therewith is a delay actuation switch 48 also situated on the front face of the control panel. The delay actuation switch is connected to delay control means 50 positioned within the control panel. The delay control means is adapted for allowing the intermittent transfer of power to the pump and fan upon the depression of the delay actuation switch. As shown in FIG. 1, the delay control means comprises an oscillator 52 and a divider 54 for providing a pulse governed by an associated RC time constant. As an option, the RC time constant may be selectively determined by way of a potentiometer 56 that is controllable via a slider switch 58 located on the front face of the control panel. By such structure, a user may select the duration between each dispensing of fragrance. Such duration preferably ranges between 5 and 30 minutes.

For controlling the transfer of power to the pump and fan, central control means 60 is positioned within the control panel and connected between the pump and fan and the manual actuation switch and the delay actuation switch and delay control means. The central control means is capable of allowing the transfer of the power to the fan and pump from at least one of the switches upon the depression thereof. In addition, it is further designed to govern each transfer of power such that each is of a constant predetermined magnitude and duration. To accomplish such, the control means ideally includes an OR gate 62 with inputs connected to the manual and delay actuation switch. Connected to an output of the OR gate is a one-shot multivibrator 64 for deploying a pulse of constant duration upon the receipt of a power signal from the switches. Such multivibrator is coupled, in turn, to a voltage controlled switch 66 which provides the necessary 12 volts to the fan and pump.

Finally, it is imperative that the manual actuation switch and delay actuation switch are both connected to an ignition of the vehicle such that they are only capable of transferring power when the vehicle is activated. To allow a user to deactivate the entire system when not desired, a power cut off switch 72 is connected between the ignition 70 and both of the switches. Such switch is ideal for when the vehicle is being used with the windows down.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A fragrance dispenser for a vehicle comprising, in combination:

a fragrance container having a cylindrical configuration with a circular top face, a circular bottom face, and a periphery formed therebetween defining an interior space, the container including a dispensing tube vertically disposed within the interior space of the container and extending through the top face thereof via a gasket, the dispensing tube having a first end situated within the interior space of the container adjacent the bottom face thereof with a plurality of apertures formed therein, the dispensing tube also having a second end positioned exterior of the container, wherein the container holds a predetermined amount of liquid fragrance and the top face of the container is removably coupled to the periphery such that the container may be refilled when necessary;

a pump connected to the second end of the dispensing tube, the pump having a dispensing nozzle connected thereto and situated below a dash of the vehicle, the pump adapted to spray the liquid fragrance from the dispensing nozzle upon the receipt of power;

a fan situated behind the dispensing nozzle for dispersing the liquid fragrance sprayed by the pump upon the receipt of power;

a control panel having a rectangular configuration and situated within a reach of a user of the vehicle;

a fragrance low level detection means including a liquid switch situated within the interior space of the container and situated a predetermined distance from the bottom face of the container adapted to open upon the lack of detection of liquid for emitting a low level signal upon the lack of detection of liquid, the fragrance low level detection means further including a light emitting diode situated on a front face of the control panel for emitting a light upon the receipt of the fragrance low level signal;

a manual actuation switch situated on the front face of the control panel for allowing the single and immediate transfer of power to the fan and pump upon the depression thereof;

a delay actuation switch situated on the front face of the control panel and connected to delay control means positioned within the control panel, the delay control means adapted for allowing the intermittent transfer of power to the pump and fan upon the depression of the delay actuation switch, wherein the delay control means comprises an oscillator and a divider for providing a pulse governed by an associated RC time constant and the RC time constant may be selectively determined by way of a potentiometer that is controllable via a slider switch located on the front face of the control panel, wherein a duration between each dispensing of fragrance is between 5–30 minutes; and central control means positioned within the control panel and connected between the pump and fan and the manual actuation switch and the delay actuation switch and delay control means, the central control means adapted to allow the transfer of the power to the fan and pump from at least one of the switches upon the depression thereof and further govern each transfer of power such that they are of a constant predetermined magnitude and duration, wherein the central control means includes an OR gate with inputs connected to the manual and delay actuation switch, a one-shot multivibrator connected to an output of the OR gate for deploying a pulse of constant duration upon the receipt of a power signal from the switches, and a voltage controlled switch coupled to the multivibrator for providing necessary voltage to the fan and pump;

said manual actuation switch and said delay actuation switch both connected to an ignition of the vehicle for being capable of transferring power only when the vehicle is activated.

* * * * *